United States Patent [19]
De Remigis

[11] 3,936,189
[45] Feb. 3, 1976

[54] ON-LINE SYSTEM FOR MONITORING THE COLOR, OPACITY AND BRIGHTNESS OF A MOVING WEB

[75] Inventor: Joseph De Remigis, New Market, Canada

[73] Assignee: Sentrol Systems Ltd., Downsview, Canada

[22] Filed: Mar. 13, 1974

[21] Appl. No.: 450,894

[52] U.S. Cl. .................. 356/73; 356/199; 356/176; 356/178; 356/244; 356/256; 250/226; 209/111.6
[51] Int. Cl.² .................... G01J 3/50; G01N 21/30
[58] Field of Search ................... 356/173–195, 356/42, 243, 244, 215, 236, 73, 199; 250/226

[56] References Cited
UNITED STATES PATENTS

| | | | |
|---|---|---|---|
| 1,950,975 | 3/1934 | Davis | 356/236 |
| 2,882,785 | 4/1959 | Biesele, Jr. | 356/73 |
| 3,455,637 | 7/1969 | Howard | 356/199 |
| 3,476,482 | 11/1969 | Howard et al. | 356/199 |

OTHER PUBLICATIONS

Van Brimer et al., Tappi, Vol. 50, No. 2, pp. 65A–70A, Feb., 1967.
Wickstrom, Tappi, Vol. 55, No. 11, Nov. 1972, pp. 1588–1591.

*Primary Examiner*—Robert J. Webster
*Attorney, Agent, or Firm*—Shenier & O'Connor

[57] ABSTRACT

An on-line system for continuously monitoring the color, opacity and brightness of a moving web of paper or the like in which an optical shoe providing black and white backgrounds spaced in the direction of movement of the web supports a portion of the web below and generally in registry with an optical head made up of a light integrating sphere for directing light from a source onto the web over the shoe and a plurality of elongated sensing units mounted in the upper portion of the sphere and including a centrally located brightness measuring unit oriented generally perpendicularly to the web toward a point over the black background, four circumferentially spaced color tristimulus sensing units, each of which is oriented at an angle to the axis of the central unit so as to be directed at the same point as is that unit and a sixth opacity sensing unit angularly oriented with respect to the axis of the central unit so as to be directed toward a point over the white background spaced downstream of the first point. The optical shoe, in addition to the black and white backgrounds normally positioned below the web, carries respective black and white standards adapted selectively to be moved into cooperative relationship with the head when the system is off web to permit the detectors to be standardized without removing the sensing head from the installation.

2 Claims, 5 Drawing Figures

ON-LINE SYSTEM FOR MONITORING THE COLOR, OPACITY AND BRIGHTNESS OF A MOVING WEB

BACKGROUND OF THE INVENTION

One of the most difficult quality control problems in the paper making industry, for example, has been the monitoring of color, brightness, and opacity within specified limits in the course of manufacture of the paper. The color and brightness of a white surface and its opacity greatly influence its appearance to the human eye and the intensity of any color applied to it. As a matter of fact, the interrelationship between color and opacity is so intimate as to make the monitoring of one without the other virtually meaningless.

In the prior art, the problem heretofore has been that of efficiently controlling the three variables of color, opacity and brightness. The only approach available is the use of individual sensors for measuring these variables. Such a system not only is awkward and complicated but also fails to provide consistent quality.

I have invented an on-line system for continuously monitoring the color, opacity and brightness of a moving web, which system overcomes the defects of systems of the prior art. My system permits of the accurate reproduction of any shade and any color. My system permits of self-standardizing for all three variables without removal from the line on which it is used. My system has color, brightness and opacity stability with a sensitivity surpassing that of the human eye. Short and long term color variations in an installation employing my system are less than those discernible by the human eye. My system can be used reliably over the entire spectrum of color and does not require recalibration when major grade changes are made. It permits of decreased use of dyes and better control of costly fillers in the manufacture of a colored web such as paper or the like. My system puts out signals which are specially adapted for use in a digital computer for efficient on-line control to desired standards.

SUMMARY OF THE INVENTION

One object of my invention is to provide an on-line system for continuously monitoring the color, opacity and brightness of a moving web which system overcomes the defects of arrangements of the prior art.

Another object of my invention is to provide a system for continuously monitoring the color, opacity and brightness of a moving web which permits of the accurate reproduction of any shade and any color.

A further object of my invention is to provide an on-line system for continuously monitoring the color, opacity and brightness of a moving web which system permits of standardization without removing the system from the line on which it is used.

A further object of my invention is to provide an on-line system for monitoring the color, opacity and brightness of a moving web with a sensitivity which surpasses that of the human eye.

Yet another object of my invention is to provide an on-line system for continuously monitoring the color, opacity and brightness of a moving web to produce a product the short and long term color variation of which is less than that which is discernible by the human eye.

A still further object of my invention is to provide an on-line system for continuously monitoring the color, opacity and brightness of a moving web which is reliable over the entire spectrum of colors and which does not require recalibration when major grade changes are made.

A still further object of my invention is to provide an on-line system for continuously monitoring the color, opacity and brightness of a moving web which produces output signals which are especially adapted for use in a digital computer for efficient on-line control of the product being produced.

Other and further objects of my invention will appear from the following description.

In general my invention contemplates the provision of an on-line system for continuously monitoring the color, opacity and brightness of a moving web in which an optical shoe located beneath and supporting a part of the web being monitored provides black and white backgrounds spaced in the direction of movement of the web for cooperation with an optical head having a light integrating sphere for directing illumination from a source onto the web over the optical shoe and incorporating a plurality of axially elongated sensing units, located generally at the top of the sphere, including a central brightness sensing unit oriented generally perpendicularly to the plane of the web toward a point over the black background, four color tristimulus value sensing units each of which is oriented at an angle to the axis of the central detector so as to be directed toward the same point as is the central detector and an opacity sensing unit angularly oriented with reference to the axis of the central detector so as to be directed toward a point spaced downstream from the central detector and over the white background provided by the optical shoe. The shoe supports respective white and black standards adapted selectively to be rotated into position below the sensing head with the system on-line but off-web for standardization of the various measuring units.

BRIEF DESCRIPTION OF THE DRAWINGS

In the accompanying drawings which form part of the instant specification and which are to be read in conjunction therewith and in which like reference numerals are used to indicate like parts in the various views:

FIG. 5 is a graph illustrating the amounts of the three International Commission on Illumination primaries required to match a unit amount of energy having a particular wavelength.

DESCRIPTION OF THE PREFERRED EMBODIMENT

Figure 1:
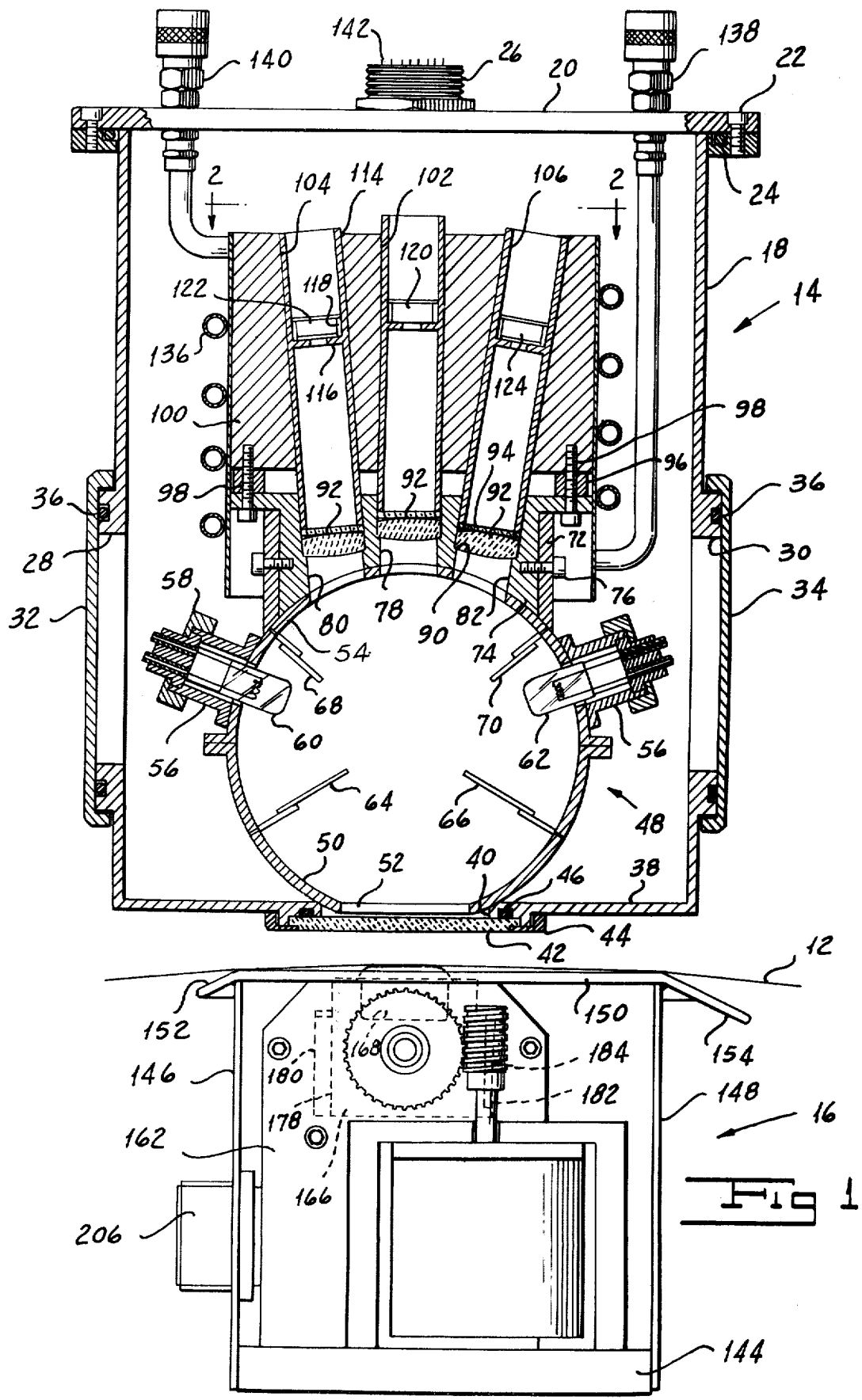
FIG. 1 is a side elevation with parts broken away and with other parts shown in section of my on-line system for continuously monitoring the color, opacity and brightness of a moving web.

As is known in the art, any color can be matched by mixing various amounts of three primary colored lights such, for example, as red, green and blue. The only limitation as to what colors can be used as primary colors is that in a given trio no pair can be mixed in any proportion to match the third. Selecting, for example, the three International Commission on Illumintion (ICI) primary colors of red, green and blue, in general color at a particular wave length $\lambda$ can be expressed as:

1. $\overline{C_\lambda} = r_\lambda \overline{R} + g_\lambda \overline{G} + b_\lambda \overline{B}$ where $r\lambda$ is the number of units of the color R necessary to make up the color $\overline{C}_\lambda$ and so forth.

At certain wave lengths, because of human eye response, it is not possible to obtain a match unless one of the primary colors first is mixed with the monochromatic light at the wave length in question and the mixture is then matched by using the other two colors as:

2. $\overline{C}_\lambda + r_\lambda \overline{R} = g_\lambda \overline{G} + b_\lambda \overline{B}$ so that some numbers may be negative.

A color can be represented by the expression:

3. $C = \sum_\lambda f_\lambda C_\lambda$ where $f\lambda$ is the amount of energy at the wave length and $C\lambda$ is the color of the monochromatic light at wave length $\lambda$.

There has been developed a positive system for color measurement for representing an observer's response to a new red, green and blue stimulus. This system is represented by the graph of FIG. 5 in which the red response is represented by $\bar{x}$, the green response by $\bar{y}$, and the blue response by $\bar{z}$. The second lobe on the red curve $\bar{x}$ response occurs in the blue as a result of the fact that it was not possible to match the monochromatic light at those wave lengths without adding one of the primary lights to the monochromatic light being matched. The tristimulus color coordinates of a color $C_\lambda$ such as represented in equation (3) are given by:

4. $X = \sum_\lambda f_\lambda \bar{x}_\lambda$
5. $Y = \sum_\lambda f_\lambda \bar{y}_\lambda$
6. $Z = \sum_\lambda f_\lambda \bar{z}_\lambda$ where $\bar{x}_\lambda$, $\bar{y}_\lambda$, and $\bar{z}_\lambda$ are the color coordinates of $C_\lambda$ read from the curves of FIG. 5.

For a particular object, $f\lambda$ is the amount of light reflected in wave length $\lambda$ and is given by the product of the reflectance $R\lambda$ and incident energy $I\lambda$ at the wave length in question. The tristimulus coordinates of the object are:

7. $X = \int R(\lambda) I(\lambda) \bar{x}(\lambda) d\lambda$
8. $Y = \int R(\lambda) I(\lambda) \bar{y}(\lambda) d\lambda$
9. $Z = \int R(\lambda) I(\lambda) \bar{z}(\lambda) d\lambda$ where $I(\lambda)$ is the spectral distribution of the incident light.

For a detector having a spectral density $D(\lambda)$ for a given region, the output signal is:

10. $S = \int R(\lambda) I(\lambda) F(\lambda) d\lambda$

In my system I employ four light sensitive detectors to measure the tristimulus values of the light falling on the detectors. I provide the detectors with computer fitted filters to duplicate the ICI tristimulus functions $X_{red}$, $X_{blue}$, Y and Z. That is to say, if $D(\lambda) = \overline{X}(\lambda)$, the signal output of the detector is X and so forth. I achieve this result by providing filters having transmittances $TX(\lambda)$, $TY(\lambda)$, and $TZ(\lambda)$ so that:

11. $D(\lambda) TX(\lambda) \alpha \bar{x}(\lambda)$ and so forth, with the constants determined by reading a sample with known tristimulus values. In practice, I employ two detectors for the $\overline{X}$ response, one peaking in red and the other peaking in blue in accordance with FIG. 5.

In any optical measuring system, spectral distribution of the source of light is critical, since the measured values X, Y and Z for a surface are different for different illuminations. The difference between a standard source having a prescribed spectral distribution and the source actually used can be accounted for by building the filters such that:

12. $I(\lambda) D(\lambda) TX(\lambda) \alpha \bar{x}(\lambda) I'(\lambda)$ and so forth, where $I'(\lambda)$ is the standard and $I(\lambda)$ the actual source. Thus the ouputs of my detectors are:

13. $S I \alpha X_{red} = \int R(\lambda) I(\lambda) T \bar{x}_{red} D(\lambda) d\lambda = k_1 R(\lambda) I'(\lambda) \bar{x}_{red}(\lambda) d\lambda$ and so forth.

Opacity is the physical property of paper which determines the degree to which paper will mask an object which it covers. One definition of opacity is constant ratio opacity which is the ratio of $R_b$ to $R_{89}$, where $R_b$ is the luminous reflectance of a single sheet of paper as measured with a white backing plate which has a luminous reflectance of 89 percent. Luminous reflectance is defined as the ratio of the reflected light signal produced by a detector with a $\bar{y}$ type response, for example, under standard conditions of illumination to the reflected light signal from the same detector for a perfectly white sample under standard illuminating conditions. Since the denominator of the definition is itself a defined quantity, any $\bar{y}$ detector can be calibrated using a standard of known luminous reflectance to read per cent reflectance directly. In a color measuring system, the coordinate Y is by definition luminous reflectance. As will be more fully explained hereinbelow, in my system I use this color coordinate measurement together with the output of a detector directed onto the web over a white background to compute opacity.

Brightness is defined as the reflectance at a source wave length of 457 nanometers. In my system, I employ a sixth detector which views the sample over a black backing to provide an output proportional to sample brightness.

With the foregoing in mind, referring now to the drawings, my on-line system indicated generally by the reference character 10 is adapted to measure the color, opacity and brightness of a web 12 of paper or the like. The system 10 includes an optical sensing head, indicated generally by the reference character 14, disposed above the web 12 and an optical shoe, indicated generally by the reference character 16, disposed below the head. Any suitable means (not shown) may be provided for mounting the head and shoe for movement out of associated relationship with the web 12.

The optical sensing head 14 includes a housing 18 to which a top plate 20 is secured by any suitable means such as by screws 22 into sealing engagement with a gasket 24 extending around the top of the housing. Top plate 20 carries a mounting stud 26 adapted to be secured to the head support (not shown). I provide the housing 18 with respective access openings 28 and 30 normally closed by covers 32 and 34 which engage gaskets 36 to seal the access openings 28 and 30.

The base 38 of the housing 18 is provided with an opening 40 over which a window 42 is secured. For example, a frame 44 carrying the window is adapted to be threaded onto a flange on the bottom 38 around opening 40 and into sealing engagement with a gasket 46.

The sensing head 14 includes a light integrating sphere indicated generally by the reference character 48 located inside housing 18 and made up of a lower half 50 formed with an opening 52 which registers with the window 42 and with an upper half 54 secured in operative relationship with the lower half in any suitable manner.

I secure respective bulb mounting tubes 56 over openings in the upper sphere half 54. Caps 58 assembled on the tubes 56 hold bulbs 60 and 62 and their associated mounts in position in the tubes 56 to direct light into the interior of the sphere 48. I provide the lower sphere half 50 with a pair of light deflectors 64 and 66 and provide the upper sphere half 54 with light deflectors 68 and 70 for ensuring proper distribution of light from the sources 60 and 62 within the sphere while at the same time preventing the detectors to be described hereinbelow from being directly illuminated by the sources 60 and 62. While any suitable sources may be employed, preferably I employ two 50 watt tungsten filament lamps for the lamps 60 and 62.

The head 14 includes a lens housing support 72 carried by the upper half 54 of the light integrating sphere. I mount the lens and filter housing 74 within the support 72 and secure it in position by any simple means such as by screws 76. I form the housing 74 with a central bore 78 the axis of which extends diametrically of the sphere and generally perpendicularly of the web 12 being monitored. A second bore 80 in the housing 74 is directed at an angle of 5° to the central bore so that the axis thereof is directed onto the web at a point approximately 14 mm downstream from the point at which the axis of the central bore 78 intersects the web. In addition to the bores 78 and 80, I provide four bores 82, each of which is directed at an angle of 10° to the axis of bore 78 and is so located that its axis intersects the web at the same point as does the axis of the central bore 78. I form each of the bores 78, 80 and 82 with a shoulder 90 along the length thereof. A plurality of lenses 92 located in the respective bores rest on the shoulders 90. As will be more fully explained hereinbelow, as required I provide filters 94 in the bores 82 which filters may, for example, be located above the lenses 92.

A spacer ring 96 spaces a heat sink 100 above the lens and filter housing 74. I provide any suitable means such, for example, as screws 98 for securing the heat sink 100 to a peripheral flange on the housing 74.

Figure 2:
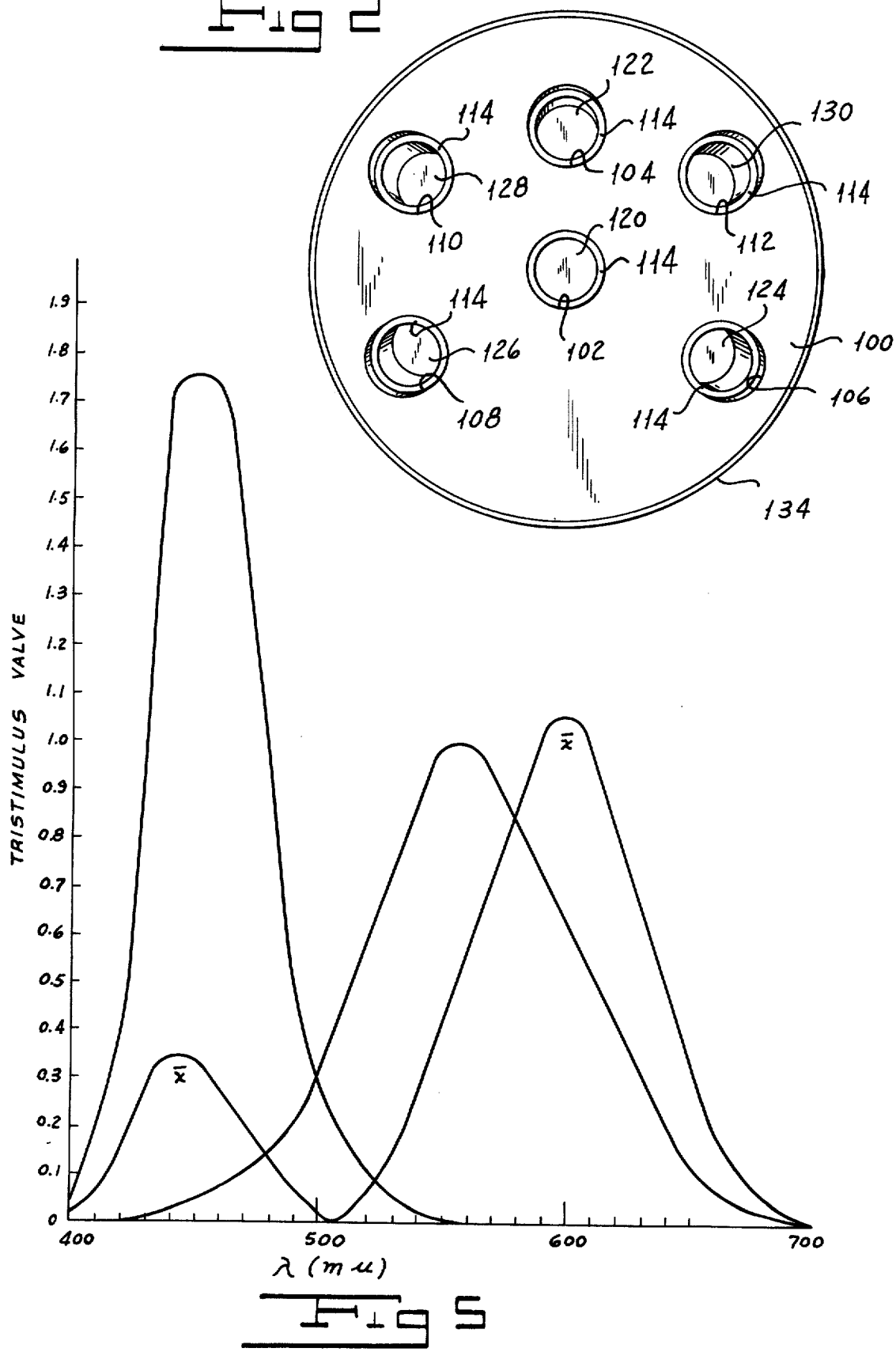
FIG. 2 is a top plan view of a portion of the optical sensing head of my system taken along the line 2—2 of FIG. 1.
Figure 3:
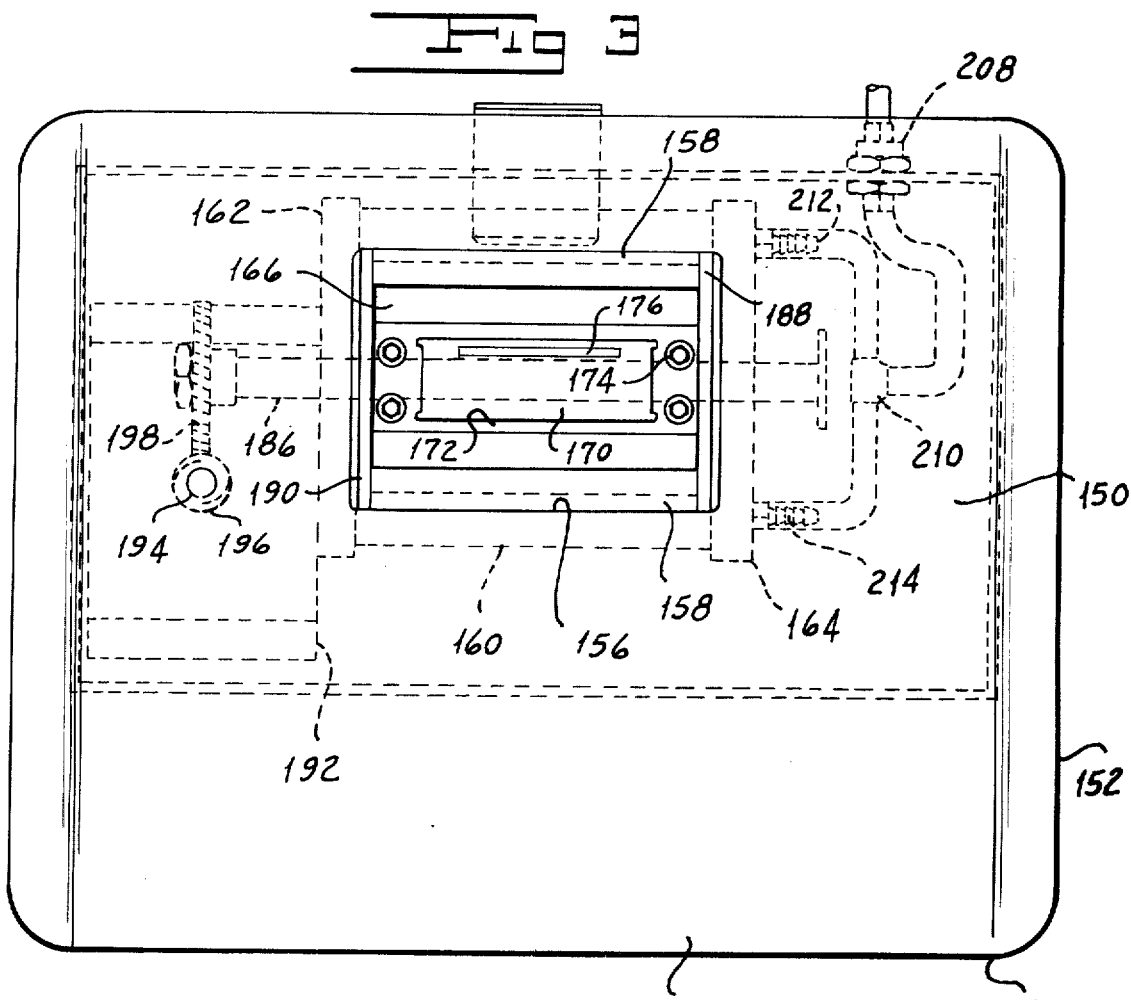
FIG. 3 is a top plan view of the optical shoe of my on-line system for continuously monitoring the color, opacity and brightness of a moving web.
Figure 4:
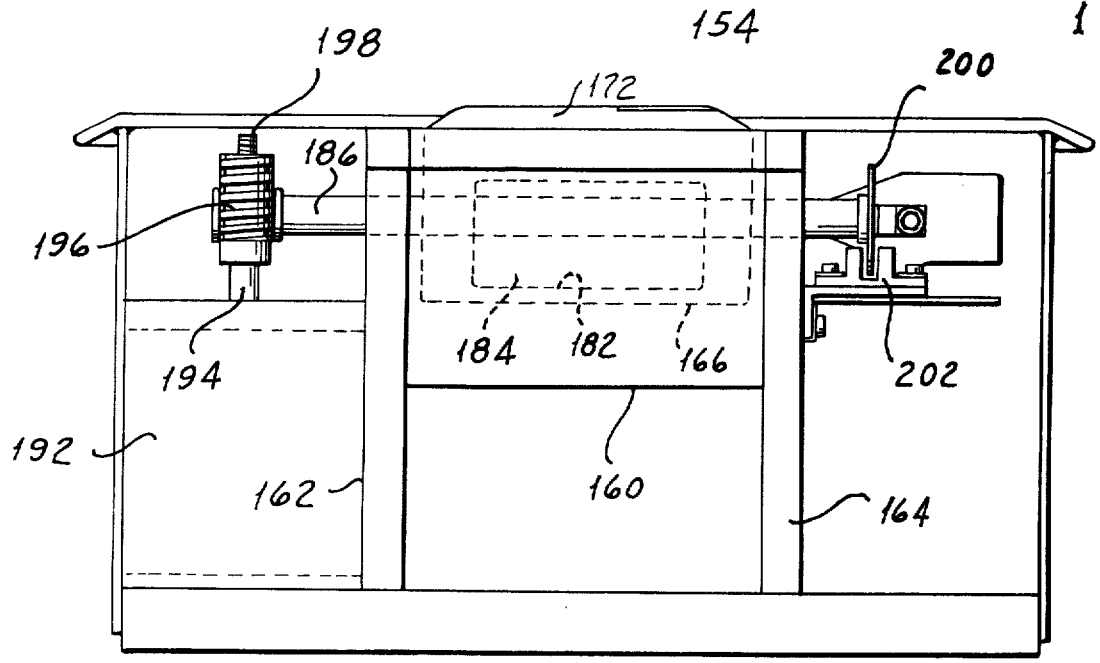
FIG. 4 is an end elevation of the optical shoe of my on-line system for continuously monitoring the color, opacity and brightness of a moving web.

I form the heat sink 100 with respective bores 102, 104, 106, 108, 110 and 112, which respectively register with the bore 78, the bore 80 and the four bores 82, when the heat sink is assembled on the housing 74. The relative location of the various bores is more clearly shown in FIG. 2 This location of the bores has been distorted in the showing of FIG. 1 for purposes of exposition.

I position a detector supporting tube 114 in each of the bores 102, 104, 106, 108, 110 and 112. Each detector tube 114 includes an annular detector locating flange 116 formed with an opening through which reflected light can be focused on the associated detector. Respective spacers 118 located in the tubes above the flanges 116 position a central brightness detector 120 in the tube in bore 102, an opacity detector 122 in the tube in bore 104, and respective $x_{red}$, $x_{blue}$, $y$ and $z$ color tristimulus value detectors 124, 126, 128 and 130 in the bores 106, 108, 110 and 112. Preferably, I provide a heat shield 134 surrounding the assembly of the lens and filter housing 74 and heat sink 100. A cooling coil 136 around the heat shield 134 is adapted to be supplied with a cooling fluid through an inlet 138. An outlet fitting 140 carries the fluid away from the coil 136. Preferably, the mounting stud 26 includes a plug 142 for making electrical connections to the various detectors of the system.

As is pointed out hereinabove, the color tristimulus value detectors 124, 126, 128 and 130 are provided with respective computer fitted filters 94 to duplicate the ICI tristimulus response functions $x_{red}$, $x_{blue}$, Y and Z. I provide the opacity detector 122 with a filter 94 which gives the detector a Y response. The central detector is provided with a filter 94 passing light at 457 nanometers.

The optical shoe 16 includes a frame base plate 144 and end plates 146 and 148. The shoe 150 which may, for example, be welded or otherwise secured to the end plates 146 and 148 includes a downwardly extending flange 152 around three sides thereof and a relatively longer entry flange 154 along which the web is guided as it moves onto the upper surface of the shoe. An opening 156 in the shoe 150 below the window 42 in the head 14 is provided with edge seals 158.

The optical shoe 16 includes a housing 160 provided with end plates 162 and 164 secured to the housing in any suitable manner. A mounting block 166 disposed within the housing 60 is formed with an optically black cavity 168 over which I mount a quartz shoe 170 carried by a frame 172. Screws or the like may be used to secure the frame 172 to the block 166. It will readily be appreciated that the portion of the quartz shoe 170 located over the cavity 168 provides the black background discussed hereinabove. In provide to provide the white background I apply a white stripe 176 to the quartz shoe 170. I so locate the stripe 176 that the detector 122 is directed toward the portion of the web which overlies the stripe 176. A first recess 178 in one side of block 166 receives one of the standards such, for example, as the black standard 180. A recess 182 in the other side of the block receives the other standard such, for example, as the white standard 184. As the white standard I may, for example, employ a mirror.

A shaft 186, rotatably supported in bearings 188 and 190 at the sides of the opening 156 carries the block 166 for rotation therewith. In the on-web position of my system in which the quartz shoe 170 is located below the web, the block 166 engages the seals 158 so that the interior of the housing 160 is sealed against the entry of foreign matter.

A stepping motor 192 having a shaft 194 is adapted to be energized to drive a worm 196 in engagement with a worm wheel 198 carried by shaft 186 for rotation therewith. The end of shaft 186 remote from the worm wheel 198 carries a coded disc 200 which cooperates with a photon-coupled interrupter module such, for example, as a module No. H13A1 manufactured and sold by the General Electric Company. As is known, such a module includes a solid state lamp adapted to illuminate a photo transistor. Disc 200 is coded in any suitable manner known to the art to control the light from the lamp to the transistor to control the motor so as to position the black or white standard under the sensing head as desired.

When, in a manner to be described, one of the standards is to be positioned in cooperative relationship with the sensing head, I pressurize the interior of the housing 160 to prevent the entry of extraneous material therein. For this purpose, I provide an air inlet 208 connected by a tee 210 to fittings 212 leading into the housing 160. A plug 206 provides the necessary electrical connections to the optical shoe 16.

Before setting my system into operation, I first standardize in the following manner. For purposes of exposition, the respective detectors 124, 126, 128, 130, 120 and 122 will be designated as D1 through D6. For standardization, the head 14 and shoe 16 are first retracted off-web. Next, motor 192 is energized and, under the control of disc 200 and the associated photon-coupled interrupter module 202, rotates to a position at which the black standard 180 is in position below the head 14. At the same time, any suitable means (not shown) can be operated to admit fluid under pressure to the inlet 208 to pressurize the housing 160 to inhibit the entry of any foreign matter into the housing. When this has been done, the outputs of the respective detectors, which can be designated BD1 to BD6, are measured and recorded. Next, again under the control of the coded wheel 200, the white standard 184 is rotated into position below the head 14. Pressure to the housing 160 is maintained. The outputs of the respective detectors, indicated as WD1 to WD6, are measured and recorded. With the BD and WD measured values conversion factors for transforming the detector voltages to the measured variables can be calculated. The tristimulus and brightness values for the white standard are fixed constants $X_s$, $Y_s$, $Z_s$ and $B_s$ for the system. Using these standards and the voltages measured during standardization the conversion factors for the tristimulus values can be calculated as:

14. $FX = X_s/[(WD5-BD6)+K(WD3-BD3)]$
15. $FY_1 = Y_s/(WD4-BD4)$
16. $FZ = Z_s/(WD1-BD1)$

For brightness, I use the expression:
17. $FB = B/(WD5-BD2)$ and for opacity the expression:
18. $FY_2 = Y_s/(WD5-BD5)$ where K is a fixed constant for the system determined along with the other constants when the system is calibrated.

The on-line opacity measurement $Y_1/Y_2$ can be converted to The American Pulp and Paper Institute (TAPPI) Standard by calibrating the system according to the equation 19. Opacity (TAPPI Standard) = $A+B(Y_1/Y_2)$
where A and B are fixed constants determined experimentally using several standards of known opacity. I have proved Equation (19) to be valid over an opacity range of 50 to 98.

TAPPI brightness standard is defined as the reflectance of 457 nanometer light by the sample backed by several sheets of the same paper. Owing to the fact that this is a practical impossibility for an on-line system, I calibrate my system using the equation:

20. Brightness (TAPPI Standard = C.Reflectance at 457 nanometers where C is a fixed function of opacity for the system determined by using samples of known brightness. The validity of Equation (20) has been determined experimentally.

In use of my system, after the standardization procedure described above has been carried out, I first energize the motor 192 to rotate the mounting block 166 back to a position at which it forms a seal with the edge seals 158 and at which the quartz shoe 170 is disposed below the detector head 14. Next, the head 14 and the shoe 16 are moved into an on-sheet position with the shoe supporting a portion of the sheet at a slightly elevated position below the sensing head 14. The head 14 may, for example, be positioned one-half inch above sheet 12. Under these conditions, the central brightness detector 120 and the color tristimulus detectors 124, 126, 128 and 130 all are oriented at the same spot on the web over the black cavity 168. Detector 122 which is to afford an indication of opacity is oriented toward a point approximately 14 mm downstream from the point at which the other detectors are oriented and over the white stripe 176. The outputs of detectors 124 and 126 modified by the conversion factor of Equation (14), provide the $X_{red}$ and $X_{blue}$ measurements. The outputs of detectors 128 and 130 modified, respectively, by the conversion factors of Equations (15) and (16) give the tristimulus Y and Z measurements. The output of detector 122 modified by the conversion factor of Equation (18) together with the output of detector 128 modified by the conversion factor of Equation (15) are combined in accordance with Equation (19) to give a measurement of TAPPI opacity. The TAPPI standard of brightness measurement is made by modifying the output of the detector 120 by the conversion factor C.

Signal outputs from the respective detectors 120, 122, 124, 126, 128 and 130 can be fed directly to a computer set up to give the desired measurements and to control the production process in response to deviation of the measured values from the desired values. It will be seen that I have accomplished the objects of my invention. I have provided an on-line system for continuously monitoring the color, opacity and brightness of a moving web. My system overcomes defects of arrangements of the prior art. My system permits of accurate reproduction of any shade and any color. It permits of standardization without removing the system from the line on which it is used. It has a sensitivity which surpasses that of the human eye. It permits of the production of a product the short and long term color variation of which is less than that which is discernible by the human eye. It is reliable over the entire spectrum of colors and does not require recalibration when major grade changes are made. It takes into account the intimate relationship between color opacity.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what I claim is:

1. In an on-line system for continuously and simultaneously monotoring the color and opacity and brightness of a moving web including in combination, a sensing head disposed over said web, means on said head for illuminating a portion of said web below said head, an optical shoe disposed below the illuminated portion of said web, said shoe providing spaced black and white background within said illuminated portion of the web, a brightness detector unit, an opacity detector unit, a plurality of color detector units, each of said detector units having an optical axis, means mounting said brightness detector unit and the respective color detector units on said head with their optical axes directed toward said illuminated portion over said white background and means mounting said opacity detector unit on said head with its axis directed toward said illuminated web portion over said black background to permit simultaneous measurements of color and opacity and brightness to be obtained, said optical shoe comprising block having a plurality of sides, means on a first side of said block providing said black and white backgrounds, a white standard carried by a second side of said block, a black standard carried by a third side of said block, and means mounting said block for movement selectively to position one of said sides in cooperative relationship with said sensing head.

2. Apparatus as in claim 1 in which said block mounting means comprises a housing formed with an opening registering generally with said sensing head, means normally positioning said block with said first side registering with said opening and with said block in sealing relationship with the periphery of said opening, means for selectively positioning said block with said second side adjacent to said opening and with said third side adjacent to said opening, and means for pressurizing said housing when said second side and said third side are positioned adjacent to said opening.

* * * * *